United States Patent
Zahavi et al.

(10) Patent No.: US 6,735,274 B1
(45) Date of Patent: May 11, 2004

(54) CLINICAL SCREENING CT SYSTEMS

(75) Inventors: Opher Zahavi, Hof-Hacarmel (IL); Simha Levene, Hanegev (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/182,786

(22) PCT Filed: Feb. 15, 2000

(86) PCT No.: PCT/IL00/00092

§ 371 (c)(1),
(2), (4) Date: Aug. 1, 2002

(87) PCT Pub. No.: WO01/60258

PCT Pub. Date: Aug. 23, 2001

(51) Int. Cl.[7] .................................................. G21K 5/00
(52) U.S. Cl. .............................. 378/15; 378/4; 378/193
(58) Field of Search ........................... 378/15, 20, 193, 378/194, 197, 198, 7, 19

(56) References Cited

U.S. PATENT DOCUMENTS

| | | | |
|---|---|---|---|
| 4,298,800 A | 11/1981 | Goldman | |
| 4,637,040 A | 1/1987 | Sohval et al. | |
| 4,689,809 A | 8/1987 | Sohval | |
| 4,829,549 A | 5/1989 | Vogel et al. | |
| 4,961,208 A * | 10/1990 | Okada | 378/18 |
| 5,170,439 A | 12/1992 | Zeng et al. | |
| 5,228,069 A | 7/1993 | Arenson et al. | |
| 5,247,556 A * | 9/1993 | Eckert et al. | 378/4 |
| 5,305,363 A | 4/1994 | Burke et al. | |
| 5,574,763 A * | 11/1996 | Dehner | 378/17 |
| 5,708,691 A | 1/1998 | Zmora | |
| 5,862,198 A | 1/1999 | Samarasekera et al. | |
| 5,966,422 A | 10/1999 | Dafni et al. | |
| 6,459,756 B1 * | 10/2002 | Tam et al. | 378/15 |
| 6,463,122 B1 * | 10/2002 | Moore | 378/65 |

FOREIGN PATENT DOCUMENTS

| | | |
|---|---|---|
| EP | 0 495 137 | 7/1992 |
| WO | WO 91/07131 | 5/1991 |

* cited by examiner

Primary Examiner—David V. Bruce
Assistant Examiner—Hoon Song

(57) ABSTRACT

A computerized tomographic imaging system (31) including a vertical movement arrangement (32, 35) for moving gantry of said system vertically while rotating about the object being imaged (44) to provide a helical scan.

19 Claims, 9 Drawing Sheets

CLINICAL SCREENING CT SYSTEMS

RELATED APPLICATIONS

This application is a U.S. national filing of PCT Application No. PCT/IL00/00092, filed Feb. 15, 2000 and published in English as WO 01/60258.

FIELD OF THE INVENTION

This invention is concerned with medical diagnostic imaging systems, and more particularly with computerized tomographic (CT) systems, particularly such systems used for clinical screening of patients and potential patients.

BACKGROUND OF THE INVENTION

The present invention pertains to CT scanning systems utilizing X-ray radiation for generating images of the interior regions of human patients. It will be appreciated by those skilled in the art that the present invention will also find application in conjunction with industrial CT systems used for quality assurance and the like.

In general, CT systems comprise an X-ray source and X-ray detectors for detecting the X-rays after they have passed through a subject or object. The X-ray source and associated detectors, in what are known as third generation CT systems, rotate together around the subject. In what are known as fourth generation CT systems, the X-ray source rotates about the subject being examined while the detectors are stationary and surround the subject being imaged.

In the past, CT systems have been used for detailed studies of symptomatic and sickly patients. However, to a greater extent than ever, examinations referred to as screening examinations are made for asymptomatic and healthy patients on the theory that an ounce of prevention is worth a pound of cure. Thus, if malfunctioning of an organ in a patient can be detected in its very early stages, then a complete cure is much more likely. To provide the capability of detecting health problems in early stages, the images have to be sufficiently detailed to indicate health problems. Accordingly, screening examinations ideally should provide for acquiring 2-dimensional and 3-dimensional images using helical scans.

Presently, in general, systems that provide helical scanning, use X-ray sources that traverse the patient horizontally. That is, the patient is disposed horizontally on a patient support such as a bed, and the X-ray source rotates about the patient and the bed while the bed moves horizontally. The necessity of rotating around the patient plus the bed increases the size of the system. In addition, the source and associated paraphernalia are operating against gravity for a large portion of each rotation and thus the system requires more power and sturdier components, all of which increase the size and cost of the CT systems.

Presently, there are no CT systems available that are designed primarily for screening and nonetheless provide helical scanning. An ideal screening system should be relatively small and inexpensive, and therefore should ideally fit into medical centers and clinics where most of the screening examinations take place. To assure maximizing the discovery of latent health problems, the CT screening apparatus should be capable of conducting helical scans.

Of course, any CT system that is reduced in size and capable of conducting scanning, including helical scanning, whether or not it is sufficiently inexpensive for screening, would be useful.

The system described herein provides helical scans in a vertical direction. Scanning systems, wherein the scanning apparatus is positioned by vertical movement, have been known in the past. However such scanning systems did not teach or make obvious the use of vertical scanning, and certainly not for providing helical scans in a simple and elegant manner. Vertical positioning for CT scans are shown, for example, in PCT application US90/05821, published under publication no. WO91/07131, and the contents of that application are hereby incorporated herein by reference. This prior art device uses the vertical movement capabilities of the scanner to position the scanner to obtain a CT image of a desired location in the patient, not for continuous scanning during vertical movement. No movement takes place during the scanning.

An example of a prior art, inexpensive CT X-ray scanner, is to be found in U.S. Pat. No. 4,829,549. However, the scanner of that patent does not do a whole body scan. It is designed to image the limbs or parts of limbs of patients and is primarily used for detection of osteoporosis. The vertical motion of the scanning parts of the system of the patent are for positioning the scanning components, and no movement takes place during scanning.

Vertical scanning is shown in U.S. Pat. No. 5,305,363. However, that patent teaches the use of a unique X-ray source, in the form of a toroidial tube. The patent does teach helical scanning, when the scan is in the horizontal direction, but it fails to teach helical scanning when the scan is in the vertical direction. More particularly, since the object of the present invention is to provide an inexpensive CT system, the '363 patent teaches in an opposite direction; since it actually provides a more expensive CT system with its unique toroidial X-ray source, which accordingly would not be at all economic for screening.

SUMMARY OF THE INVENTION

An aspect of some preferred embodiments of the present invention is to provide a smaller, but extremely efficient CT system that can be used, among other things, for screening. To reduce the size and cost of the CT system, the patient support or bed normally associated with the CT scanner is eliminated, and vertical scanning is used.

According to an aspect of some preferred embodiments of the present invention, the CT scanning system includes a gantry or CT ring that contains an X-ray source and oppositely disposed detector apparatus. The subject either sits or stands in the center of the ring, and the ring moves vertically while rotating about the patient to provide the helical scans. According to an aspect of the invention, the helical scanning movements, both vertical and rotational, are done by the source and associated detectors.

In an aspect of some preferred embodiments of the invention, a small, inexpensive X-ray tube power supply is used. It is trickle-charged between patients and discharged during the scan. The high-voltage cable, on systems using such a power supply, does not have to be flexible, since the charged power supply is mounted directly upon rotating, vertically moving CT ring. Thus, the high-voltage cable that trickle-charges the high-voltage power supply is disconnected during the actual scan and only connected between scans.

In an aspect of some preferred embodiments of the invention, view data are recorded in a memory on the moving gantry during the scan, thereby eliminating the need for expensive data transmission apparatus. The memory, such as a hard disc, is replaced between patients or can be read out between patients, and reconstruction is carried-out on a separate console. The separate console can be used for a multiplicity of scanners, or the separate console can be used for the regular patients in the hospital during the day, and used for the screening of patients in the evening.

In another preferred embodiment, the system is installed in a mobile screening vehicle, and the image is reconstructed and evaluated at a central public health clinic, where a single sophisticated processing work station may be installed to serve a multiplicity of such mobile units.

Accordingly, preferred embodiments provide a CT system that is inexpensive, occupies a small space and is light in weight, but is capable of effective helical scanning. These advantages make it ideal for screening using multiple stations or for use as a mobile unit.

In accordance with a preferred aspect of the invention, a computerized tomographic imaging system is provided, which includes a gantry or CT ring defining a central bore surrounding the subject being imaged. At least one X-ray source is mounted on said gantry for emitting X-rays. X-ray detectors are also mounted on the gantry, oppositely disposed from said at least one X-ray source, to detect X-rays that have traversed said subject The gantry moves on vertically-extending, helically-arranged rails, causing the X-ray source to describe a helix to provide a helical scan of the subject, as the gantry travels over the vertically-extended, helically-arranged rails. Alternatively, the gantry moves vertically while the at least one X-ray source rotates about the patients to provide helical scans.

In third generation systems, detectors are mounted opposite the at least one X-ray source and arranged to rotate with the at least one X-ray source about the subject. In fourth generation systems, only the at least one X-ray source rotates. Detectors are mounted on the gantry surrounding the subject.

In a preferred embodiment of the invention, the detectors, which within the scope of the invention may be single slice, multi-slice or large area detectors, acquire imaging data during said helical scan. An image reconstructor is provided for reconstructing images from said imaging data, and display means display the reconstructed images.

There is thus provided in accordance with a preferred embodiment of the invention a computerized tomographic (CT) imaging system comprising: a gantry defining a central bore surrounding an object being imaged; at least one X-ray source mounted on the gantry for emitting X-rays; X-ray detectors mounted on said gantry to detect X-rays from said source that traverse said object; and a helical movement arrangement for moving the gantry vertically while rotating the at least one X-ray source about the object being imaged to provide a helical scan. In a preferred embodiment of the invention, the at least one X-ray source is affixed to said gantry; and the helical movement arrangement includes vertically extending helically-arranged rails to provide a helical scan of the subject as the gantry travels over the rails. Preferably, the arrangement further includes coupling units attached to said gantry for coupling said gantry to said rails. Preferably, the arrangement includes a rack on said rails and wherein said coupling units include gears meshing with said rack. In a preferred embodiment, the gears are motorized. Preferably, the detectors are arranged to acquire imaging data during said helical scan.

Preferably, the arrangement includes: a vertical movement arrangement for moving said gantry with said at least one X-ray source vertically; and a rotating movement arrangement wherein the at least one X-ray source rotates within said gantry about said object while said gantry is moving vertically. Further, preferably the X-ray detectors are fixedly mounted opposite said at least one X-ray source to receive X-rays that have traversed the object and to move with said at least one X-ray source. In a preferred embodiment of the invention, an image constructor that reconstructs images from said imaging data; and a monitor is also provided that displays said reconstructed images.

In a preferred embodiment of the invention, the CT imaging system includes a memory that receives said acquired image data to enable the provision of images at a central imaging data processing and display center. Preferably, the said memory is located on the gantry. Further, preferably a power pack is mounted on said gantry for powering the components on said gantry during the helical scan. Still further, preferably the power pack includes high voltage capacitors. Preferably, a trickle charger for charging said power pack when not in use is provided. Preferably, the capacitors are in parallel during the charging and in series during use.

In a preferred embodiment of the invention, the at least one X-ray source includes more than one X-ray source mounted on said gantry. Preferably, the at least one X-ray source comprises a single focal spot X-ray source. Alternatively, the at least one X-ray source includes multiple focal spots.

In a preferred embodiment of the invention, the X-ray detectors comprise a single row of X-ray detectors. Alternatively, the X-ray detectors comprise multiple rows of detectors. Preferably, the X-ray detectors comprise area detector arrays.

There is further provided a method for providing computerized tomographic (CT) images comprising: directing X-ray beams at an object; detecting X-ray beams that have traversed the object; and moving the X-ray beams vertically while rotating about the object being imaged to provide a helical scan. Preferably, the X-ray beams are moved along a set helical path. Preferably, the X-ray beams are rotated while moving them vertically to describe a helical scan. Still further, preferably gravity is used to move the X-ray beams. Alternatively or additionally, preferably motorized equipment to move the X-ray beams.

In a preferred embodiment of the invention, imaging data are acquired during said helical scan Preferably, images are reconstructed from the imaging data; and the reconstructed images are displayed. Preferably, the image data are converted to memory and used to generate images at a central imaging data processing and display center.

In a preferred embodiment of the invention, a single focal spot X-ray source is used for directing X-rays at an object. Alternatively, a multiple focal spot X-ray source is used for directing said X-ray beams at an object Preferably, X-ray detectors that comprise a single row of X-ray detectors are provided. Further, preferably X-ray detectors that comprise multiple rows of detectors are used. Alternatively, large area detector arrays are provided.

BRIEF DESCRIPTION OF THE DRAWINGS

The features and objects of the invention believed to be novel are set forth with particularity in the appended claims. The invention itself, however, as to apparatus, organization and method of operation, together with further objects and advantages thereof may best be understood by reference to the following non-limiting description, taken in conjunction with the accompanying drawings, in which:

DETAILED DESCRIPTION

Figure 1:
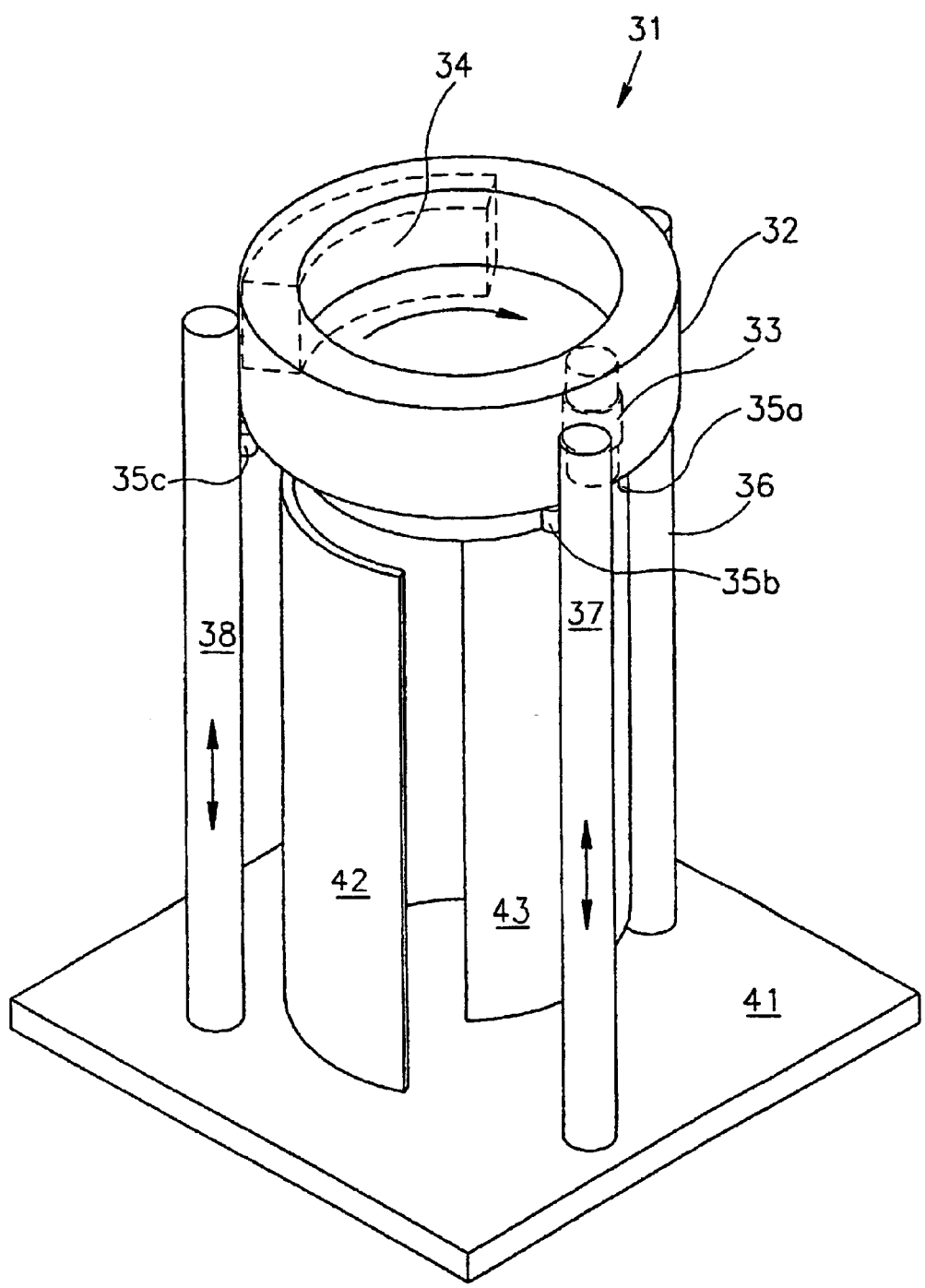
FIG. 1 is a pictorial view of a preferred embodiment of the present invention.

The pictorial showing of CT system 31 of FIG. 1 is comprised of a CT gantry or ring 32, mounted with its axis vertically disposed. Mounted on the CT ring are at least one X-ray source 33 and detector apparatus indicated at 34. The CT ring 32 is designed to rotate about its axis as it travels vertically downwardly or upwardly.

In third generation systems, both the at least one X-ray source and the oppositely-disposed detectors are connected to the gantry to rotate together about the subject. In fourth generation systems, the at least one X-ray source is coupled to the gantry so as to rotate with gantry about the subject; permanently-disposed detectors surround the subject. The subject or patient is located within the ring and preferably coextensive with the axis of the ring. A plurality of supports or posts st own at 36, 37 and 38 in FIG. 1 support the ring as it rotates about the patient while it moves vertically. More particularly, according to a preferred embodiment, the at least one X-ray source rotates about the patient within the ring which does not rotate. The ring with the rotating X-ray source, however, moves vertically. In third generation systems, both the at least one X-ray source and the oppositely-disposed detectors move within the ring while the ring is moving vertically. In fourth generation systems, only the at least one X-ray source rotates within the non-rotating but vertically moving ring.

Figure 4:
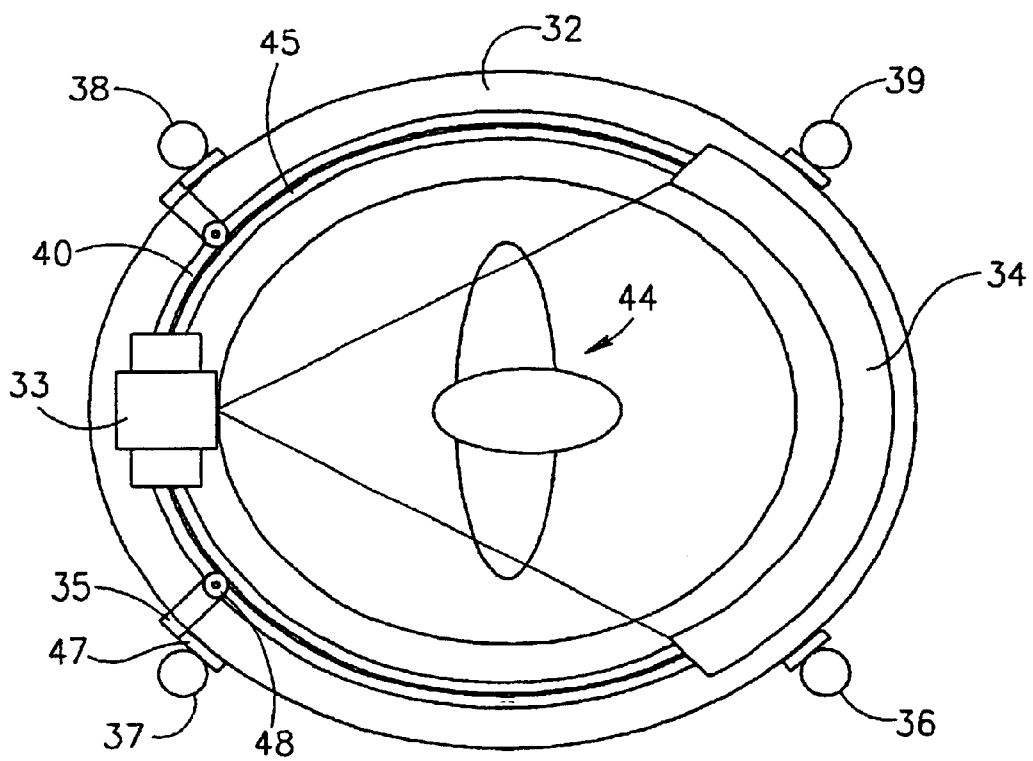
FIG. 4 is plan view of the CT system with the gantry rotating while moving vertically to perform a helical scan.
Figure 4A:
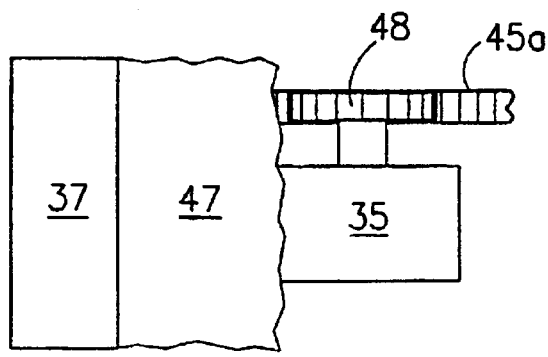
FIG. 4A is break away view showing circular and vertical racks and gear arrangements for rotating the CT ring while causing it to move vertically to thereby describe a helix.

In accordance with a preferred embodiment of the invention, the posts have racks that mesh with the gears of gear boxes such as gear boxes indicated at 35a, 35b and 35c, in FIGS. 1, 4 and 4A. The gear boxes are arranged to support the ring 32 on the rack and to cause the ring to move vertically. The gear boxes are also arranged to have gears that mesh with a circular rack to cause that rack to rotate. The circular rack is attached to the at least one X-ray source 33 to cause the X-ray source to rotate with the ring. Alternatively, the at least one X-ray source is attached to the rotating ring 32. In third generation systems, the detectors 34 are also coupled to the circular rack or to the CT ring, to cause the detectors to rotate with the at least one X-ray source.

A chamber 43 surrounds and protects the patient as the CT ring 32 moves vertically. The diameter of the chamber is smaller than the diameter of the CT ring. The system is mounted on and includes a base 41. A door to the chamber is provided at 42, enabling access to the chamber 43.

It is within the scope of the invention to provide a plurality of X-ray sources; however, when the system is to be used for screening then the most inexpensive version of the invention may be desired and that is the version with only a single X-ray source. Within the scope of the invention, an outer chamber may be provided which houses the entire system 31, including the support posts, 36, 37 and 38.

Figure 1A:
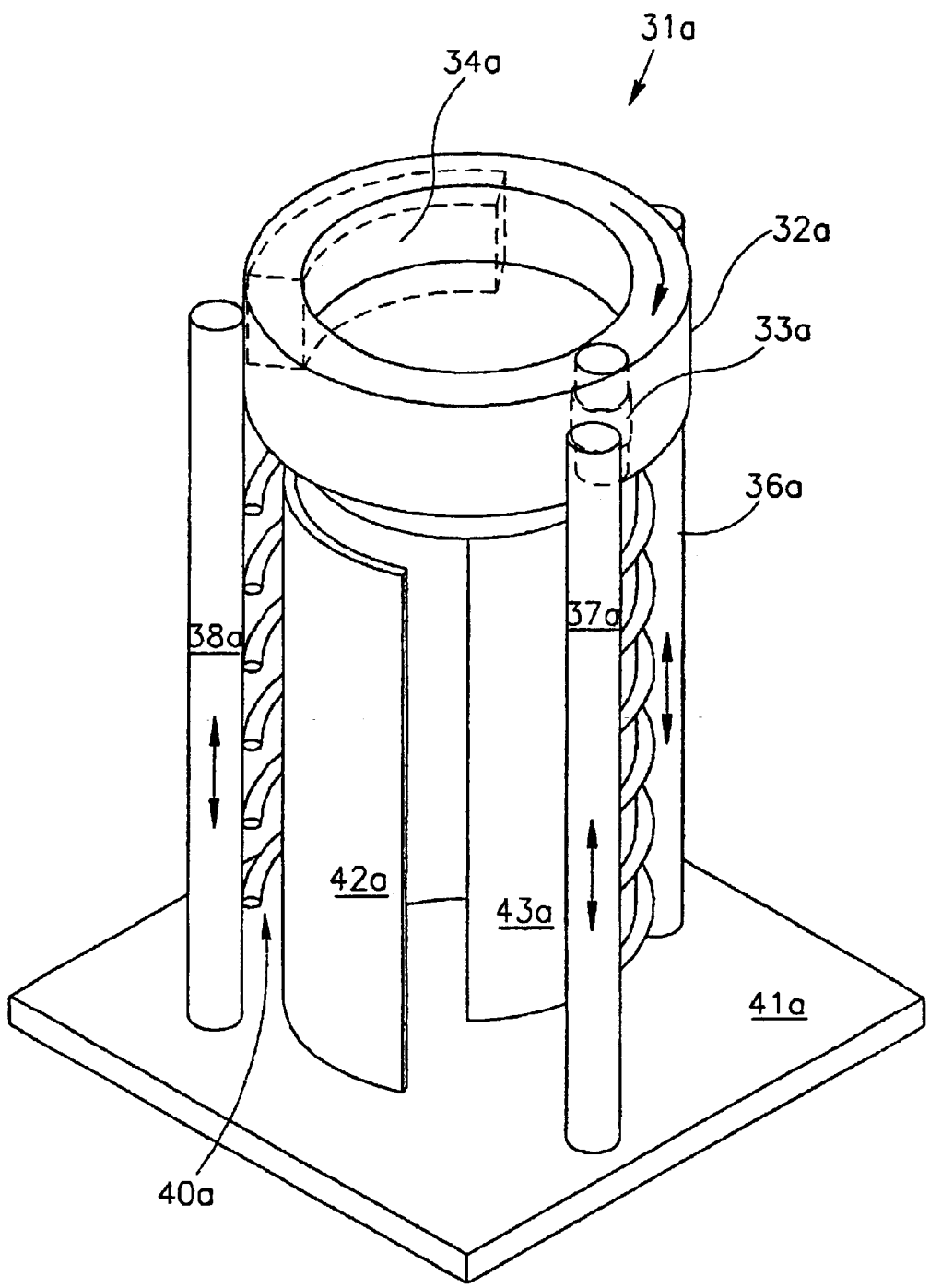
FIG. 1A is a pictorial view of another preferred embodiment of the present invention.

In the embodiment of FIG. 1A, a plurality of posts shown at 36a, 37a and 38a (a fourth post is not seen), support helically-extending rail 40a.

The ring 32a is mounted on the rail 40a to move in a general vertical direction while rotating about the patient so as to provide a helical motion relative to the subject or patient. Within the scope of the invention, the helical rotation of the CT ring is provided either by gravity or the movement is motorized.

Figure 2:
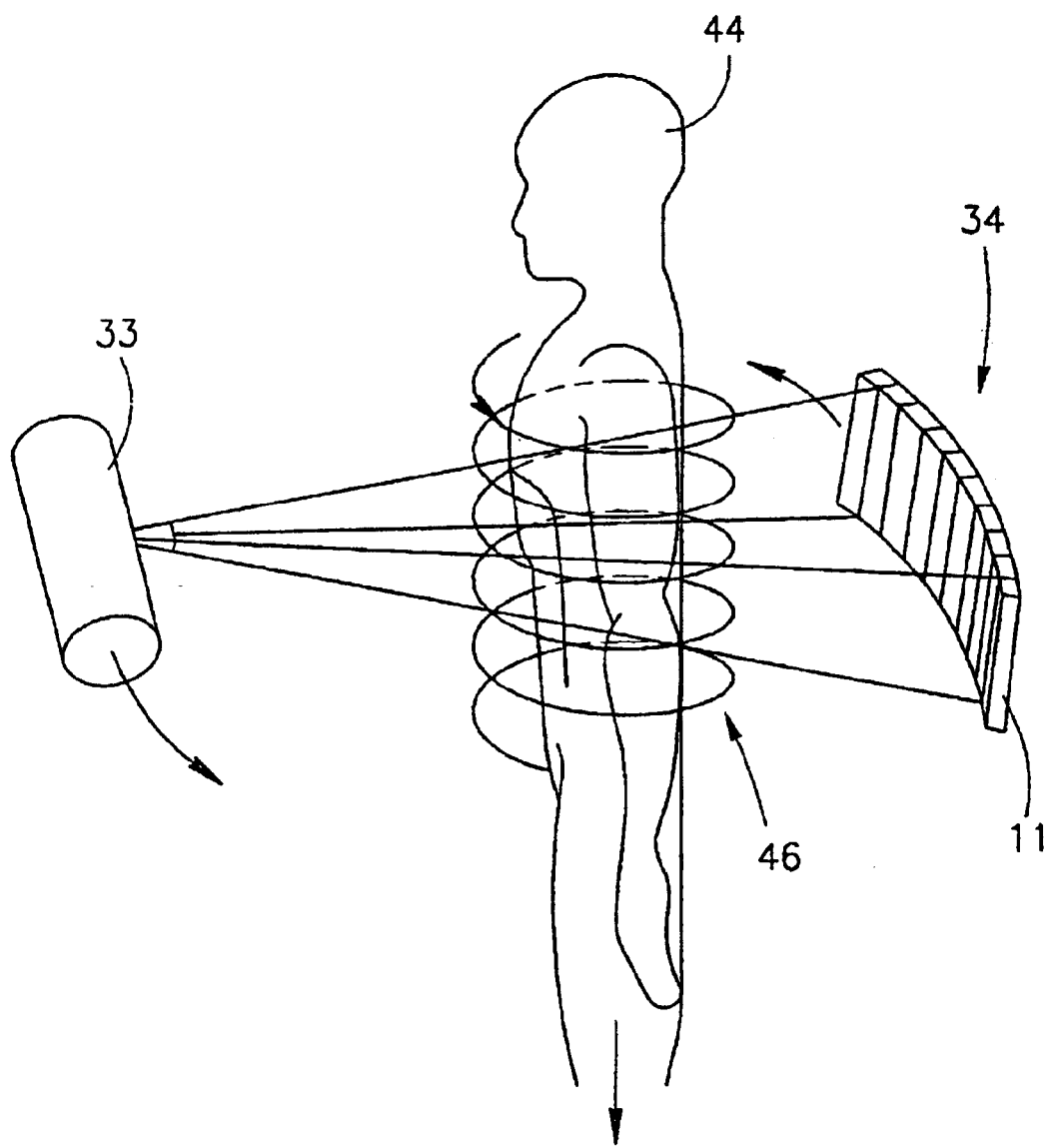
FIG. 2 is a pictorial representation of at least one X-ray source and associated detector arrangement performing a helical scan of a patient wherein the X-ray source provides an X-ray scan from a single focal point.

FIG. 2 is a pictorial showing of the at least one X-ray source 33 and the detector arrangement 34, moving vertically while rotating and providing a helical scan of the subject 44, as described in relation to FIG. 1 or 1A. The, helical scan trajectory is shown at 46 and is typically generated by an X-ray beam from a single source having a single focal point. The detector array 11 of FIG. 2 is shown as having only a single row of detector elements.

Figure 3:
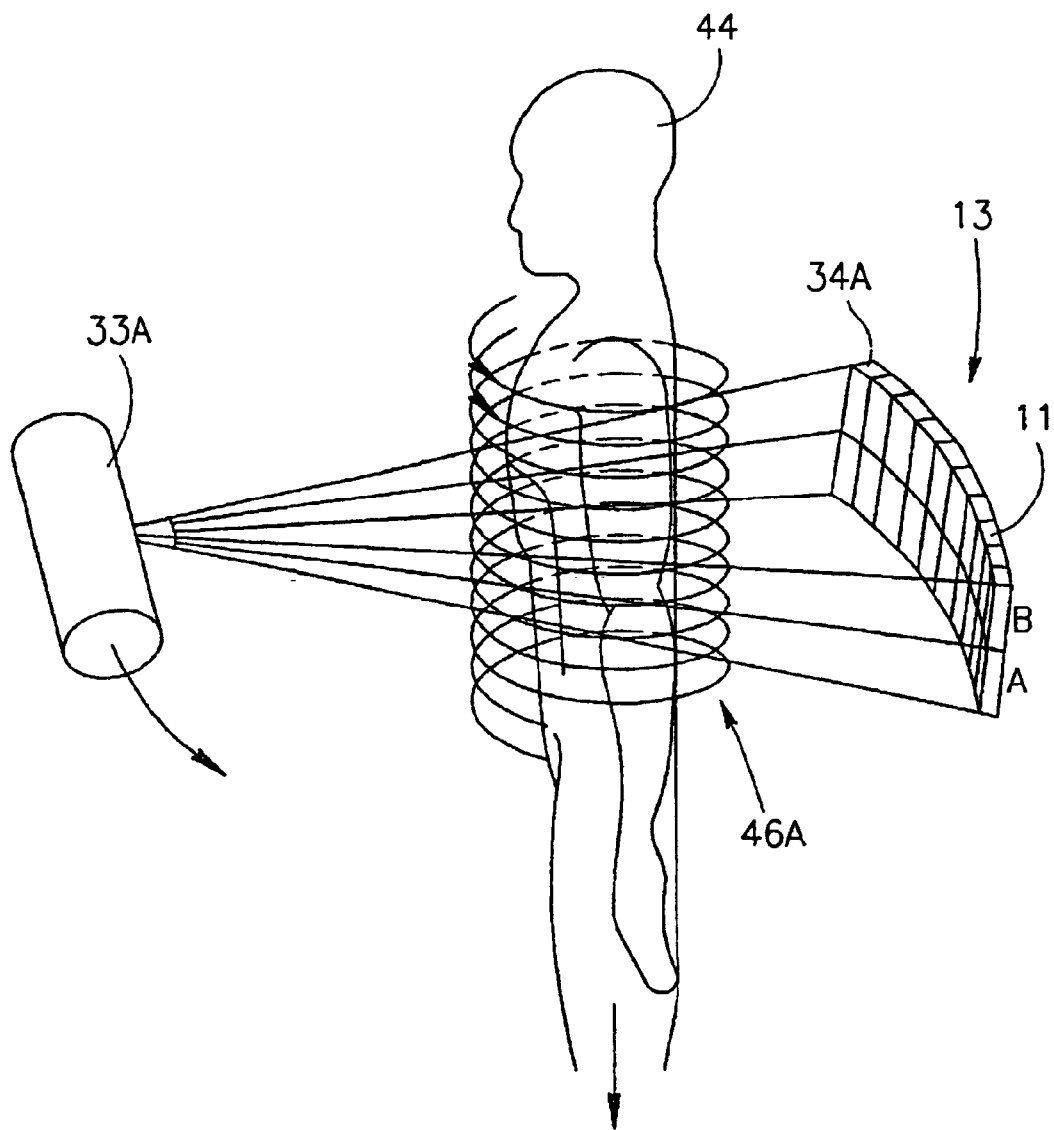
FIG. 3 is a pictorial representation of the at least one X-ray source and associated detector arrangement performing a helical scan wherein the detector arrangement comprises multiple rows of detectors, and the at least one X-ray source provides a plurality of beams emanating from a plurality of focal points.

FIG. 3 also illustrates a helical scan, as described in relation to FIGS. 1 and 1A. In the version of FIG. 3, a unit is provided wherein the X-ray source 33a contains an X-ray tube having more than one focal point with a multiplicity of X-ray beams emitted by the tube. For teachings of an X-ray source with multiple focal points see U.S. Pat. No. 4,689,809. For teachings of CT systems using X-ray sources with multiple focal points, see for example U.S. Pat. No. 4,637,040. The contents of each of the above patents are hereby incorporated herein by reference. While a single source is shown in the figures, it is within the scope of the invention to use multiple X-ray sources such as taught in U.S. Pat. No. 5,966,422, the contents of which are hereby incorporated herein by reference.

In addition to an improved X-ray source, an improved detector 34a is shown which includes a multiplicity of rows of detectors, increasing the resolution of the system. While this seems to be a more expensive version, actually, it may reduce the size of the X-ray tube and power supply, and thus the overall cost. For teaching of multiple rows of detectors see, for example, U.S. Pat. No. 5,228,069, the contents of which are hereby incorporated herein by reference. The helical scan trajectory about the subject 44 generated by beams from dual focal points is shown at 46a in FIG. 3.

The plan view of FIG. 4 shows the CT ring 32 surrounding the patient 44. In this view, the chamber 43 is omitted. The X-ray source 33 is oppositely-disposed from detector apparatus 34 to detect the X-rays that have traversed the patient 44.

In a fourth generation system, the detectors surround the patient and do not rotate, only the X-ray source rotates.

In the embodiment of FIG. 4, the ring 32 is affixed to a circular rail 45. The at least one X-ray source 33 is affixed to ring 32 either directly or through circular rail 45. In third generation systems, the detectors 34 are also affixed to the ring 32 either directly or through rail 45. Thus, the at least one X-ray source and the detectors move vertically with the ring and rotate within the vertically moving ring so that the X-rays traversing the patient 44 provide a helical scan of the patient.

As shown in FIG. 4A, the circular rail 45 includes a circular rack 45a attached to the circular rail. Attached to posts 36–39 are vertical racks such as vertical rack 47 shown with post 37, for example. The gears of a gear box 35 mesh with rack 47. Either gravity or a motor causes a drive gear 48 that meshes with the gears of the rack to rotate the circular rack 45. The circular rack 45 and consequently the ring 32 are caused to rotate during the vertical motion of ring 32 along vertical rack 47 to provide the helical scan.

Figure 5:
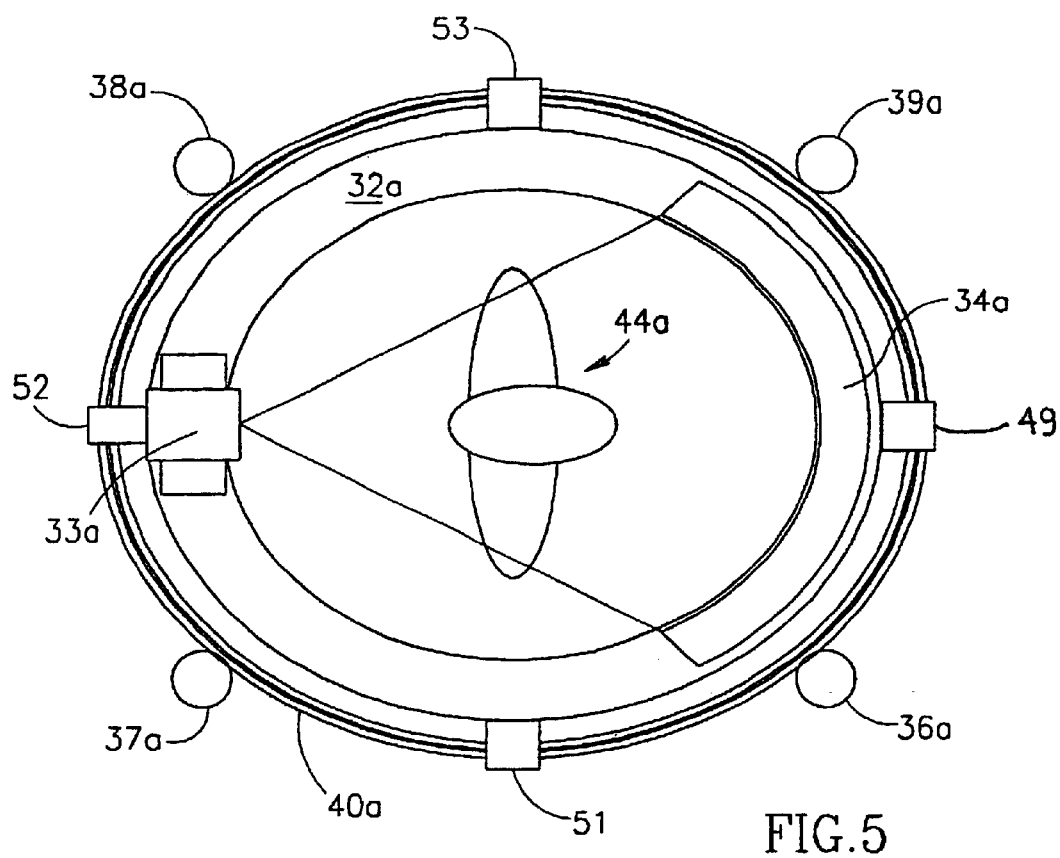
FIG. 5 is a plan view of the CT system with the gantry moving along vertically extending helically-arranged rails to provide a helical scan in accordance with a preferred embodiment of the present invention.

In the plan view of FIG. 5, the helically-extending rail 40a is affixed to support posts 36a, 37a, 38a and 39a. The CT ring 32a is attached to the rail through coupling units 49, 51, 52 and 53. In a preferred aspect of the invention, the rail includes a helical rack and the coupling units include motorized gears that mesh with the rack and propel the gantry along the helical rails. Alternatively, the coupling units include braking arrangements for controlling the descent of the gantry when gravity is used as the motivational force propelling the gantry. The gantry is raised by hand or a hoist is used when gravity is the motivating force propelling the gantry along the rails to provide the helical trajectory.

Figure 5A:
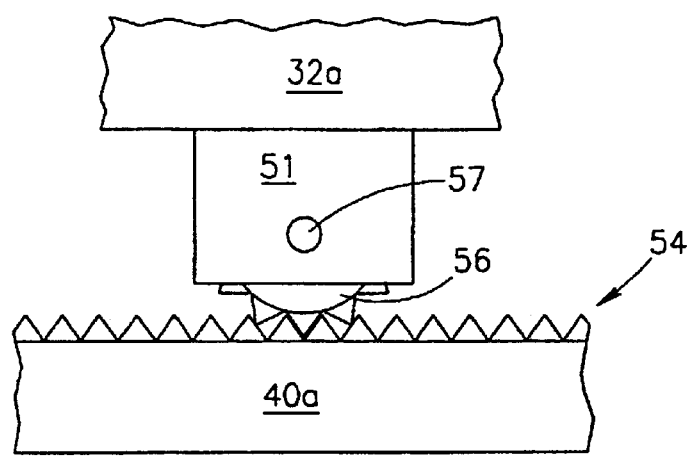
FIG. 5A is a side view showing a rack and gear arrangement for coupling the gantry to the helically-extending rail to thereby cause the gantry to describe a helix.

FIG. 5A is a side schematic view of a rack and gear arrangement for use in controlling the motion of the CT ring 32a on the rail 40a. As shown in FIG. 5A, the coupling units such as unit 51 includes a motorized gear 56. It rotates about its axis 57 and meshes with the rack 54 on rail 40a. The motorized gear is either powered by a power pack or through the use of brushes as is well known to those skilled in the art.

It should be recognized that while a gear and rack arrangements are shown for moving the CT scanning component to describe helical path, this showing is meant to be exemplary and not limiting.

Figure 6:
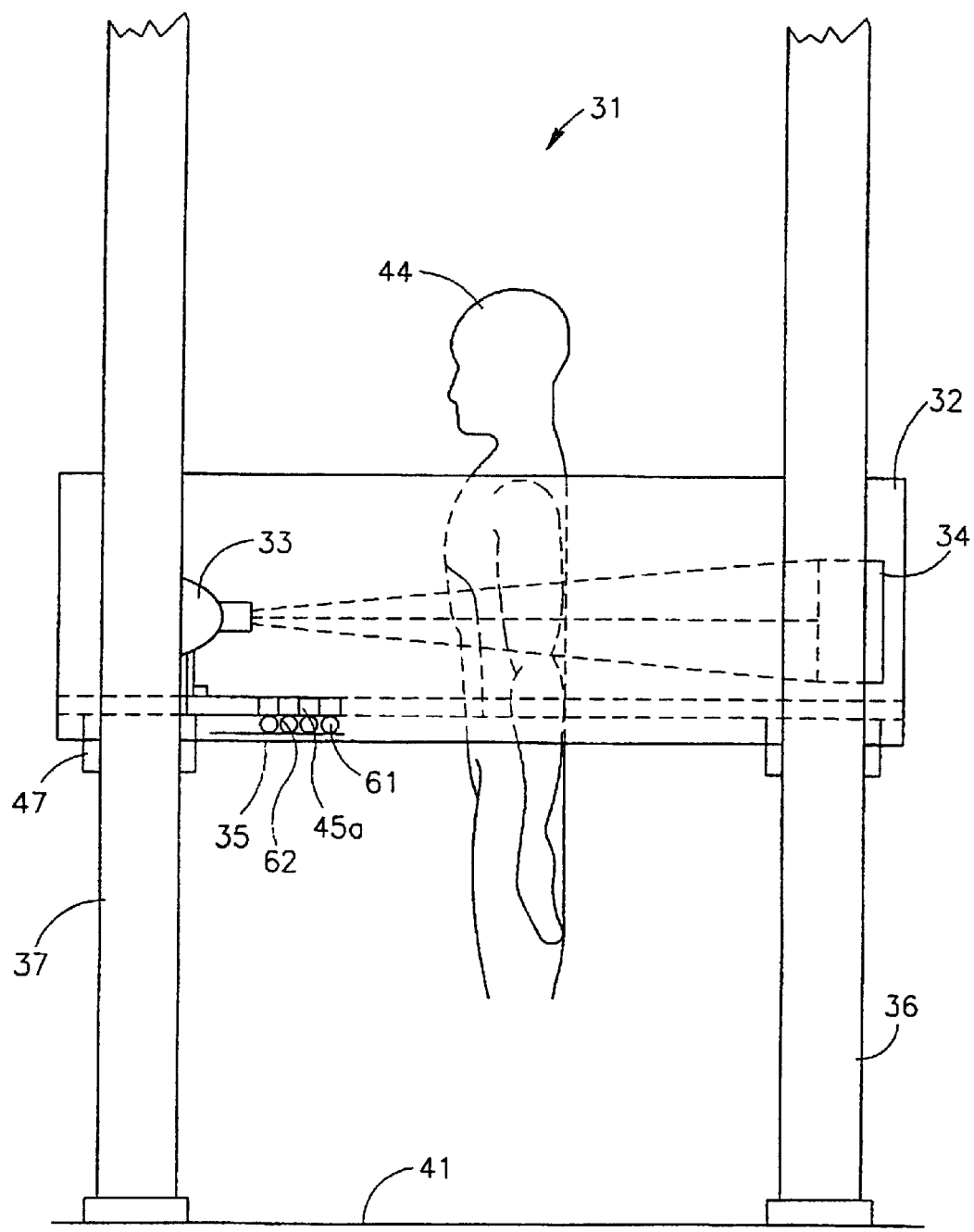
FIG. 6 is a side view showing of the CT ring traveling vertically while the at least one X-ray source rotates to provide a helical scan.

FIG. 6 is a side view showing of the screening CT system 31 of FIGS. 1, 4 and 4A. In the embodiment of FIGS. 1, 4, 4A and 6, the CT ring 32 does not ride on a helically-arranged rails.

Instead, the at least one X-ray source rotates within the ring while the ring moves vertically as indicated by the arrow. For third generation systems detectors 34 rotate with the at least one X-ray source within the ring. In fourth generation systems the detectors substantially surround the subject or patient 44 and do not rotate.

In the embodiment shown in FIG. 6, the circular rail 45 with a circular rack 45a attached thereto is shown affixed to the CT ring 32. The gears of gear boxes such as gear box 35 mesh with the vertical racks such as rack 47 attached to post. In a preferred aspect of an embodiment of the invention, gravity causes the rack to drive the gears of the gear boxes such as gear box 35. The gears of the gear box then rotate drive gear 48 which meshes with circular rack 45a and causes the at least one X-ray source to rotate while the ring is descending. In third generation systems, the detectors are also affixed to the circular rack 45 which is attached to the rotating circular rack 45a. The rail 45 and rack 45a are shown mounted on ball bearings such as bearing 61 in race 62.

In another preferred aspect of an embodiment of the invention, the gear box is motorized to drive the gears enabling controlled vertical motion in ascending as well as descending directions. When the gears are driven by a motor, then helical scanning can be accomplished while the CT ring 32 is ascending, as well as while it is descending.

Figure 6A:
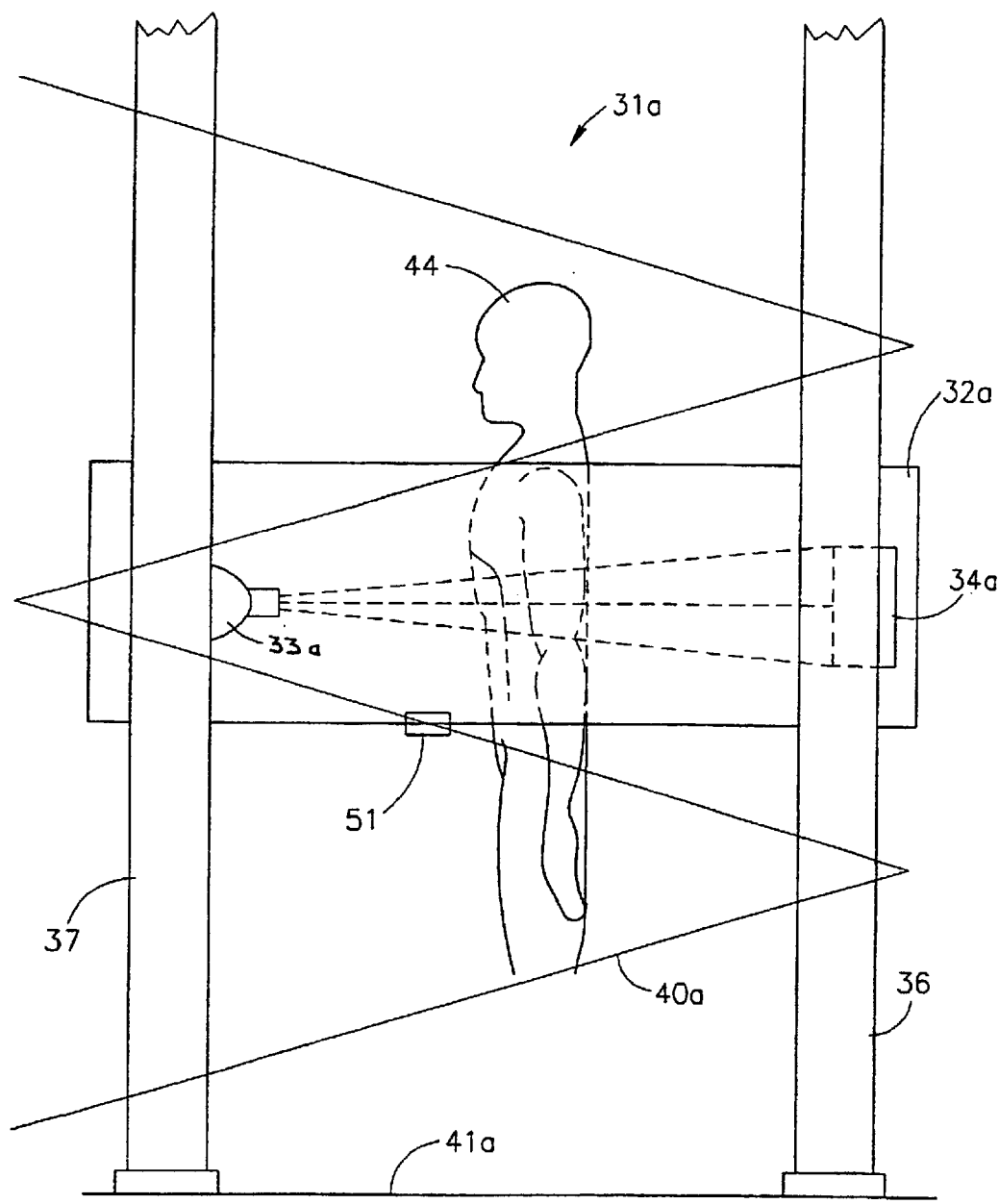
FIG. 6A is a side view showing of the CT ring traveling along the vertically-arranged helically-extending rail to provide a helical scan.

FIG. 6A is a side view showing of the screening CT system of FIGS. 1A, 5 and 5A. In those figures, the ring 32a rides on helically-arranged rails 40a. The at least one X-ray source 33a and the detectors 34a are fixed to the CT ring which surrounds the patient 44. As the CT ring 32a moves on the rails 40a, the ring and attached at least one X-ray source are caused to rotate. The combined vertical movement along the rails and rotation of the at least one X-ray source around the patient 44a provides a helical scan. In third generation system, the detector 34a rotate with the at least one X-ray source. The gear coupling between the helically-arranged rail 40a and the CT ring 32a explained in relation to FIGS. 5 and 5a is represented coupling unit 51.

Figure 7:
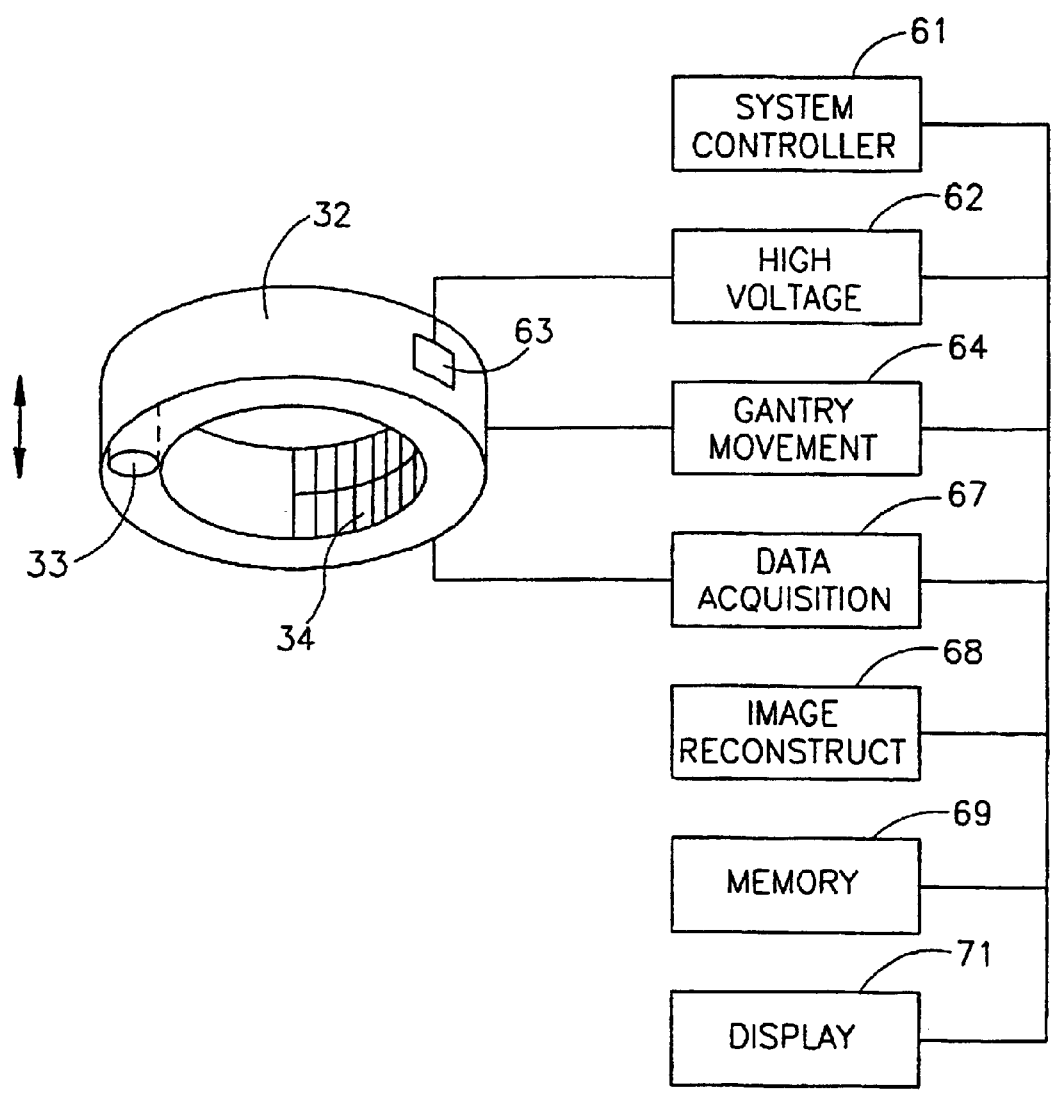
FIG. 7 is a block diagram showing of the CT ring and accompanying controls, data acquisition and processing sub-systems, in accordance with a preferred embodiment of a CT system of the present invention.

FIG. 7 is a block diagram showing of the systems 31 and 31a. Therein is shown a CT ring, or gantry 32, having an X-ray source 33 and a detector arrangement 34 shown disposed oppositely to the X-ray source. The ring rotates about the subject while moving vertically to thereby generate the helical scan. A system controller is shown at 61 to provide control and timing pulses for the system. A high-voltage power supply is indicated at 62. The high voltage power supply, in accordance with one preferred aspect of the invention comprises a charged battery pack or high-voltage capacitors, located on the ring and indicated at 63. The high-voltage capacitors are connected in parallel for charging and in series for use as is known to those skilled in the art. Alternatively, the high-voltage power is permanently connected to the ring 32 through a very flexible cable. Alternatively brushes are used in a manner well-known to those skilled in the art. When the movement is motorized, then the motor power is used to drive the ring to the top of the posts. Data acquisition then occurs both while the CT ring 32 travels up and down.

The gantry movement system is illustrated at 64. It provides braking when the ring is moved by gravity in the vertical direction, while the at least one X-ray source rotates to provide the helical scan. When the vertical motion is provided by gravity, then an elevational apparatus is provided for moving the gantry to the top of the posts, to be ready for the next scan. This elevational apparatus can be a motorized block and tackle or a hand-operated block, chain and ratchet arrangement. When a motorized vertical movement arrangement is used, then view data can be obtained during the vertical motion of the ring, regardless of whether traveling from the bottom of the post to the top of the posts or vice-versa Data acquisition is represented in block 6,7. In a preferred embodiment of the system, the acquired data are provided to a memory 50 so that the image processing can be a accomplished at a central location. The detectors 34 detect X-ray intensity after the X-rays have traversed the patient. This data are assembled and pre-processed in block 67. The pre-processed data are provided to the image reconstruction section indicated at block 68 which operates in conjunction with memory 69 to provide an image in display 71.

In operation, the patient steps into the chamber 43, where he is held still and supported in a standing or sitting position within the ring 32. The ring is then directed in a vertical movement downwards either along helically-displaced rails or in a straight vertical displacement while the at least either one X-ray source and detector rotate to provide a helical scan. Data are collected during the scan. The data are used for reconstructing the image in a well-known manner. The screening image is either displayed immediately or the data are recorded in a memory, and the memory is operated on later, for example, in a central location to provide the display.

The foregoing description of specific embodiments of the present invention is presented for purposes of illustration and description. The embodiments are not intended to be exhaustive, nor to limit the invention to the precise forms disclosed. Obviously, many modifications and variations are possible in the light of the above teaching. The embodiments were chosen and described in order to best explain the principals of the invention and the practical applications thereof to thereby enable others skilled in the art to best utilize the invention, its various embodiments and various modifications, as suited for the particular use contemplated. It is intended that the scope of invention be defined by claims appended hereto and their equivalents.

The terms "comprise", "including" or "have", or their conjugates as used herein mean "including but not necessarily limited to".

What is claimed is:

1. A computerized tomographic (CT) imaging system comprising:
    a gantry defining a central bore surrounding an object being imaged;
    at least one X-ray tube affixed to said gantry for emitting X-rays;
    X-ray detectors mounted on said gantry to detect X-rays from said at least one X-ray tube that traverse said object; and
    a helical movement arrangement for moving the gantry vertically while rotating the gantry such that at least one X-ray tube rotates the object being imaged, said helical rail arrangement including vertically extending helically-arranged rails to provide a helical scan of the object as the gantry travels over the rails.

2. The CT imaging system of claim 1 wherein the arrangement includes coupling units attached to said gantry and coupling said gantry to said rails.

3. The CT imaging system of claim 2 wherein the arrangement includes a rack on said rails and wherein said coupling units include gears meshing with said rack.

4. The CT imaging system of claim 3 wherein said gears are motorized.

5. The CT imaging system of claim 1 wherein said detectors are arranged to acquire imaging data during said helical scan.

6. The CT imaging system of claim 1 wherein said X-ray detectors are fixedly mounted opposite said at least one X-ray tube to receive X-rays that have traversed the object and to move with said at least one X-ray tube.

7. The CT imaging system of claim 5, including:
    an image constructor that reconstructs images from said imaging data; and
    a monitor that displays said reconstructed images.

8. The CT imaging system of claim 5 including a memory that receives said acquired imaging data to enable the reconstruction of images at a central imaging data processing and display center.

9. The CT imaging system of claim 8 where said memory is located on said gantry.

10. The CT imaging system of claim 1 including a power pack mounted on said gantry for powering components on said gantry during the helical scan.

11. The CT imaging system of claim 10 wherein said power pack includes high voltage capacitors.

12. The CT imaging system of claim 10 including a trickle charger for charging said power pack when not in use.

13. The CT imaging system of claim 12 wherein said capacitors are in parallel during the charging and in series during use.

14. The CT imaging system of claim 1 wherein said at least one X-ray tube includes more than one X-ray source mounted on said gantry.

15. The CT imaging system of claim 1 wherein said at least one X-ray tube comprises a single focal spot X-ray source.

16. The CT imaging system of any of claim 1 wherein said at least one X-ray tube includes a multiple focal spots X-ray tube.

17. The CT imaging system of claim 1 wherein said X-ray detectors comprise a single row of X-ray detectors.

18. The CT imaging system of claim 1 wherein said X-ray detectors comprise multiple rows of detectors.

19. The CT imaging system of claim 1 wherein the X-ray detectors comprise area detector arrays.

* * * * *